(12) United States Patent
Ingenhoven

(10) Patent No.: US 6,455,787 B1
(45) Date of Patent: Sep. 24, 2002

(54) METHOD FOR DETERMINING THE WEIGHTS OF LIQUID UNITS, WEIGHING INSERT AND WEIGHING ARRANGEMENT

(75) Inventor: Nikolaus Ingenhoven, Männedorf (CH)

(73) Assignee: Tecan Trading AG, Männendorf (CH)

( * ) Notice: Subject to any disclaimer, the term of this patent is extended or adjusted under 35 U.S.C. 154(b) by 49 days.

(21) Appl. No.: 09/707,675

(22) Filed: Nov. 7, 2000

(30) Foreign Application Priority Data

Nov. 9, 1999 (EP) ............................................ 99811023

(51) Int. Cl.[7] .................. G01G 19/52; G01G 21/28; G01P 21/00; G01F 25/00
(52) U.S. Cl. .................. 177/50; 177/180; 177/238; 177/245; 73/1.36; 73/1.74
(58) Field of Search ................................. 73/1.74, 1.36; 177/50, 180, 181, 238, 245

(56) References Cited

U.S. PATENT DOCUMENTS 5,061,639 A * 10/1991 Lung et al. .................. 436/164
5,298,978 A * 3/1994 Curtis et al. .................. 356/627

FOREIGN PATENT DOCUMENTS

| DE | 003 510 110 A1 | * 10/1986 | .................. 177/50 |
| WO | WO 95/02166 | * 1/1995 | .................. 73/1.74 |

* cited by examiner

Primary Examiner—Randy W. Gibson
(74) Attorney, Agent, or Firm—Notaro & Michalos P.C.

(57) ABSTRACT

For avoiding evaporation-related errors in the calibration of a dispenser by weighing liquid units delivered by said dispenser, an absorbent (9) in a weighing vessel (8) is arranged on a weighing pan (2) and binds the liquid units delivered onto said absorbent. To prevent falsifications occurring as a result of liquid being precipitated onto the absorbent (9), the environment of the weighing pan (2) is kept dry by a cylindrical weighing insert (10) put over said weighing pan. Said weighing insert forms a cavity (15) which receives the weighing pan (2) and is accessible from above through a longer channel (16). Both are surrounded by an inner wall (12) made of gas-permeable material, e.g. porous ceramic, through which they interact with a drying agent (18) which fills the intermediate space between the inner wall (12) and an outer wall (11) a distance away from it.

9 Claims, 2 Drawing Sheets

METHOD FOR DETERMINING THE WEIGHTS OF LIQUID UNITS, WEIGHING INSERT AND WEIGHING ARRANGEMENT

FIELD OF THE INVENTION

The invention relates to a method for determining the weights of liquid units delivered by a dispenser, and a weighing insert and a weighing arrangement for carrying out the method. The weight determination serves for calibrating dispensers, as used in chemical, biological and medical laboratories, with respect to the volume of the liquid units delivered by them.

PRIOR ART

It is known that dispensers can be calibrated on the basis of a determination of the weights of liquid units delivered by them. In the determination of the weights of very small amounts of liquid, in particular those whose volume is less than 1 $\mu$l, the fact that the surface area is very large in relation to the volume leads to a rapid relative decrease in the initial amount of liquid owing to evaporation, which falsifies the result of the weighing.

SUMMARY OF THE INVENTION

It is the object of the invention to provide a method of the generic type which permits the reliable determination of the weight of liquid units delivered by a dispenser onto a balance. This object is achieved by the features of the invention. Moreover, it is intended to provide a weighing insert and a weighing arrangement comprising such a weighing insert, which permit the method to be carried out expediently and simply.

In the method according to the invention, the effect of the liquid exchange of the amount of liquid to be weighed and of other components influencing the weighing with the environment is substantially prevented. Errors caused by evaporation or precipitation of liquid are thus eliminated. The weighing insert and the weighing arrangement comprising it enable the method according to the invention to be carried out in a simple and expedient manner.

BRIEF DESCRIPTION OF THE DRAWINGS

The invention is explained in more detail below with reference to Figures, which constitute only one embodiment.

DESCRIPTION OF THE PREFERRED EMBODIMENTS

Figure 1:
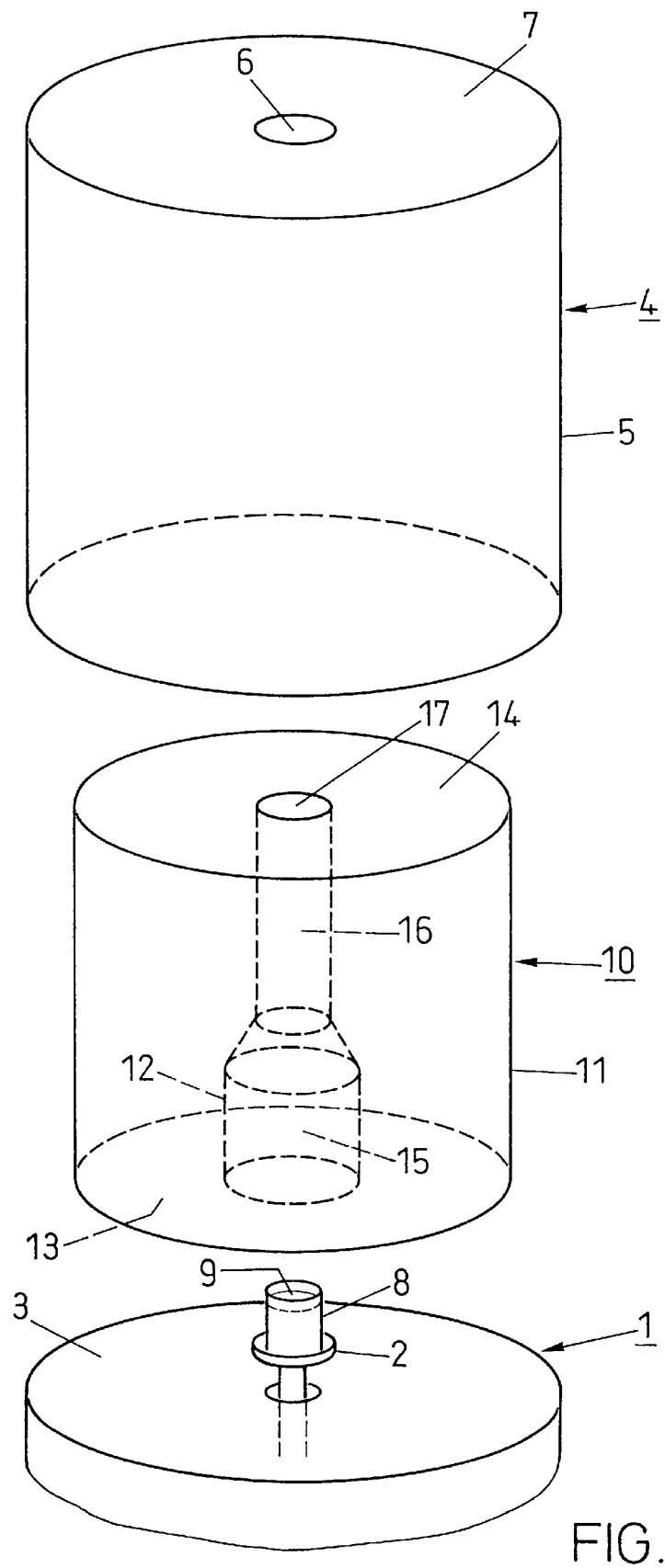
FIG. 1 shows an exploded view of a weighing arrangement according to the invention and FIG. 2 shows a vertical section through a part of a weighing arrangement according to the invention, with an inserted tip of a dispenser to be calibrated.

A balance 1, for example of the type Mettler UMT2, has a weighing pan 2 which is supported above a platform 3. The weighing pan 2 is arranged in a weighing chamber which is enclosed by a cylindrical housing 4 resting on the platform 3 and having an all-round housing wall 5 and a housing cover 7 provided with a central access orifice 6. An open weighing vessel 8, which, for example, consists of plastic or aluminium and is filled with an absorbent 9 which is suitable for binding liquid, usually water, is arranged on the weighing pan 2. It may be a drying agent to which a moisture indicator has been added, e.g. blue silica gel.

Also arranged in the weighing chamber is an essentially cylindrical weighing insert 10 which encloses the immediate environment of the weighing pan 2. It has an all-round outer wall 11 which consists of a gas- and water-impermeable material, such as, for example, glass, and an inner wall 12 which runs round the inside of said outer wall and is a distance away therefrom and comprises permeable material, e.g. porous ceramic. The outer wall 11 and the inner wall 12 are connected by an annular base 13, which rests on the platform 3, and a removable cover 14, both of which likewise consist of impermeable material, e.g. glass. A lower part of the inner wall 12 surrounds an essentially cylindrical cavity 15 which is open at the bottom and receives the weighing pan 2 with the weighing vessel 8. Access to the cavity 15 is provided by a narrower perpendicular channel 16 which connects it to a mouth 17 in the cover 14. The intermediate space between the outer wall 11 and the inner wall 12 is filled with a drying agent 18 which is suitable for absorbing and binding moisture from the air. It too may be blue silica gel.

To determine the weight of a liquid unit delivered by a dispenser, in principle the following procedure is adopted: the weighing vessel 8 filled with the absorbent 9 is placed on the weighing pan 2, after which the weighing insert 10 is put over it so that the cavity 15 receives the weighing pan 2 with the weighing vessel 8. Finally, the housing 4 is placed on top and the weighing chamber is thus closed. After an equilibration time, a tip 19 of the dispenser is immersed in a storage vessel and a little sample liquid, as a rule water, is sucked in.

Figure 2:
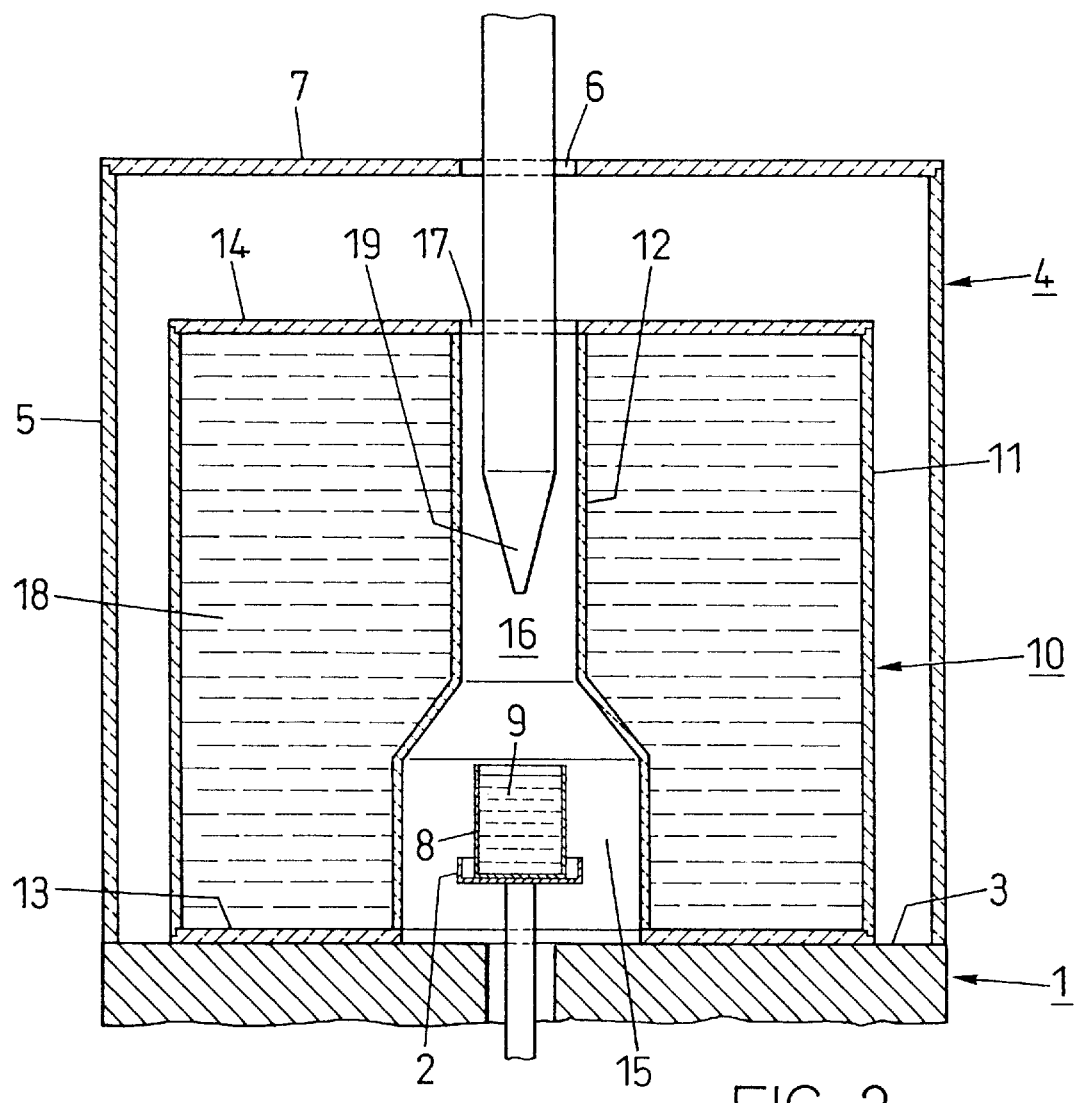

Thereafter, the tip 19 is brought over the access orifice 6 in the cover 7 of the housing 4 and is lowered through said orifice and the mouth 17 underneath in the cover 14 of the weighing insert 10 into the channel 16 (FIG. 2). Thereafter, as a rule a liquid unit—but possibly also several units—is delivered onto the absorbent 9 in the weighing vessel 8 and the weight increase thereby caused is determined.

From this and the known density of the sample liquid, the volume of the liquid unit or units delivered is finally calculated. For example, 100 such cycles, each consisting of delivery of a liquid unit and weighing, can be carried out in succession, where the volume of a liquid unit may be in general less than 100 nl, in particular between 10 nl and 100 nl. The result can then be used for adjusting the dispenser, for example for fixing the length and intensity of a control pulse for actuating a micropump thereof.

By using the absorbent 9 which binds the sample liquid, evaporation of the liquid units delivered onto the weighing pan, which might otherwise be a substantial source of measuring errors, is virtually completely prevented. The manner in which the liquid is bound is not important.

The use of a drying agent, in particular of silica gel, which physically binds the sample liquid without chemically changing it, has proved useful. After the measurements, the sample liquid can be relatively easily removed from the drying agent again, so that the latter can be reused.

To ensure that the measurements are not falsified by binding of water from the environment of the weighing pan 2 onto the absorbent 9, the environment of the weighing pan 2 must be kept dry. For this purpose, it is surrounded by relatively large amounts of drying agent, which preferably corresponds to the absorbent, and is closed off as substantially as possible together with said absorbent. The use of the weighing insert 10 is furthermore a very easily handled means.

The cavity 15 which receives the weighing pan 2 with the weighing vessel 8 with relatively little clearance interacts through the inner wall 12 with the drying agent 18, with the result that it is kept sufficiently dry. The cavity 15 and the drying agent 18 are substantially closed off from the remaining part of the weighing chamber by the gas-impermeable outer wall 11 of the weighing insert 10. The cavity 15 is accessible only through the relatively narrow channel 16, which however is likewise surrounded by drying agent with which it interacts through the inner wall 12. Virtually all water is therefore removed from air penetrating through the channel 16, before said air reaches the cavity 15.

The housing 4 which seals the weighing chamber from the outside room, apart from the narrow access orifice 6, serves as a further shield.

It has been found that the situation in the cavity 15 stabilizes relatively rapidly with respect to the water content and, after an equilibration time of between 10 min and 20 min, the tare varies only within the error of measurement of the balance—about 0.2 µg when a stone table is used for shielding against mechanical disturbances.

After delivery of a certain amount of liquid onto the absorbent 9, the latter does of course have a higher liquid content than the drying agent 18. However, when a sufficient amount of absorbent was used, diffusion of liquid from the one to the other remained in such narrow limits that no marked error resulted. In the case of total amounts of delivered liquid of up to 1 µl (e.g. 100 cycles of 10 nl each), it proved sufficient to use a weighing vessel which had a volume of 80 mm³ and was substantially filled with absorbent.

volume of 500 mm³ was sufficient even in the case of total amounts of up to 20 µl (e.g. 2 times 100 cycles of 100 nl each).

List of Reference Symbols

1 Balance
2 Weighing pan
3 Platform
4 Housing
5 Housing wall
6 Access orifice
7 Housing cover
8 Weighing vessel
9 Absorbent
10 Weighing insert
11 Outer wall
12 Inner wall
13 Base
14 Cover
15 Cavity
16 Channel
17 Mouth
18 Drying agent
19 Tip

What is claimed:

1. Method for determining the weights of liquid units delivered by dispenser, in which at least one liquid unit is delivered onto a weighing pan (2) of a balance (1) and the weight increase caused thereby is determined, characterized in that an absorbent (9) is arranged on the weighing pan (2) and the at least one liquid unit is delivered onto said absorbent while the environment of the absorbent (9) is otherwise kept dry.

2. Method according to claim 1, characterized in that the weighing pan (2) is surrounded by a drying agent (18) for keeping the environment of the absorbent (9) dry.

3. Method according to claim 2, characterized in that the environment of the weighing pan (2), including the drying agent (18), is substantially closed.

4. Weighing insert (10) for use in the method according to claim 2, characterized in that it forms a cavity (15) for receiving the weighing pan (2), which cavity is open at the bottom and is surrounded by drying agent (18) and is accessible from above through a narrower access.

5. Weighing insert (10) according to claim 4, characterized in that the access is in the form of an essentially perpendicular channel (16) starting from the cavity (15).

6. Weighing insert (10) according to claim 4, characterized in that it comprises an inner wall (12), bounding at least the cavity (15) and made of gas-permeable material, and an outer wall (11) a distance away from said inner wall, between which the drying agent (18) is arranged.

7. Weighing insert (10) according to claim 4, characterized in that it is formed rotationally symmetrically, preferably essentially cylindrically, around a perpendicular axis.

8. Weighing arrangement for carrying out the method according to claim 2, having a balance (1) which has a weighing pan (2), characterized in that it comprises a weighing insert (10) according to claim 4, whose cavity (15) receives the weighing pan (2) and an absorbent (9) arranged thereon.

9. Weighing arrangement according to claim 8, characterized in that the balance (1) comprises an essentially closed weighing chamber in which the weighing pan (2) and the weighing insert (10) are arranged.

* * * * *

UNITED STATES PATENT AND TRADEMARK OFFICE
CERTIFICATE OF CORRECTION

PATENT NO.    : 6,455,787 B1
DATED         : September 24, 2002
INVENTOR(S)   : N. Ingenhoven It is certified that error appears in the above-identified patent and that said Letters Patent is hereby corrected as shown below:

<u>Title page,</u>
Item [73], Assignee, please change the residence of the Assignee from "Männendorf (CH)" to -- Männedorf (CH) --.

Signed and Sealed this

Eighteenth Day of February, 2003

JAMES E. ROGAN
*Director of the United States Patent and Trademark Office*